(12) United States Patent
Tokumaru et al.

(10) Patent No.: US 7,547,777 B2
(45) Date of Patent: Jun. 16, 2009

(54) PENAM CRYSTALS AND PROCESS FOR PRODUCING THE SAME

(75) Inventors: Yoshihisa Tokumaru, Tokushima (JP); Akihiro Shimabayashi, Tokushima (JP)

(73) Assignees: Otsuka Chemical Co., Ltd., Osaka-shi (JP); Taiho Pharmaceutical Co., Ltd., Tokyo (JP)

( * ) Notice: Subject to any disclaimer, the term of this patent is extended or adjusted under 35 U.S.C. 154(b) by 381 days.

(21) Appl. No.: 10/574,279

(22) PCT Filed: Oct. 8, 2004

(86) PCT No.: PCT/JP2004/015299

§ 371 (c)(1),
(2), (4) Date: Mar. 31, 2006

(87) PCT Pub. No.: WO2005/035538

PCT Pub. Date: Apr. 21, 2005

(65) Prior Publication Data

US 2007/0060559 A1 Mar. 15, 2007

(30) Foreign Application Priority Data

Oct. 10, 2003 (JP) .............................. 2003-352723

(51) Int. Cl.
*C07D 499/00* (2006.01)
*C07D 499/04* (2006.01)

(52) U.S. Cl. ..................................................... 540/310
(58) Field of Classification Search .................. 540/310
See application file for complete search history.

(56) References Cited

U.S. PATENT DOCUMENTS

| 4,891,369 | A | * | 1/1990 | Torii et al. ................... | 540/310 |
| 4,895,941 | A | * | 1/1990 | Torii et al. ................... | 540/310 |
| 4,898,939 | A | * | 2/1990 | Torii et al. ................... | 540/310 |
| 4,912,213 | A | * | 3/1990 | Taniguchi et al. ........... | 540/310 |
| 4,925,934 | A | | 5/1990 | Taniguchi et al. ........... | 540/310 |
| 5,763,603 | A | | 6/1998 | Trickes ........................ | 540/310 |
| 6,660,855 | B2 | * | 12/2003 | Shimabayashi et al. ..... | 540/310 |
| 2002/0193587 | A1 | | 12/2002 | Shimabayashi et al. ..... | 540/314 |
| 2002/0193588 | A1 | | 12/2002 | Shimabayashi et al. ..... | 540/310 |
| 2004/0162277 | A1 | * | 8/2004 | Shimbayashi et al. ....... | 514/192 |
| 2009/0012287 | A1 | * | 1/2009 | Wada et al. .................. | 540/310 |

FOREIGN PATENT DOCUMENTS

| JP | 1-224379 | 9/1989 |
| JP | 8-505645 | 6/1996 |
| JP | 2002-53581 | 2/2002 |
| JP | 2002-53582 | 5/2002 |
| WO | WO 02/14325 | 2/2002 |
| WO | WO 02/092605 | 11/2002 |

* cited by examiner

*Primary Examiner*—Mark L Berch
(74) *Attorney, Agent, or Firm*—Kratz, Quintos & Hanson, LLP

(57) ABSTRACT

The present invention provides novel 2α-methyl-2β-[(1,2,3-triazol-1-yl)methyl]penam-3α-carboxylic acid benzhydryl ester (TMPB)-acetone crystals for use in the production of 2α-methyl-2β-[(1,2,3-triazol-1-yl)methyl]penam-3α-carboxylic acid 1,1-dioxide benzhydryl ester (TAZB); a process for producing the TMPB-acetone crystals comprising the steps of (A) concentrating a TMPB-containing organic solvent solution, (B) dissolving the resulting concentrate in acetone, and (C) precipitating TMPB-acetone crystals from the acetone solution thus obtained; and a process for producing TAZB comprising the step of reacting the TMPB-acetone crystals with an oxidizing agent.

10 Claims, 2 Drawing Sheets

PENAM CRYSTALS AND PROCESS FOR PRODUCING THE SAME

TECHNICAL FIELD

The present invention relates to penam crystals and a process for producing the same.

BACKGROUND OF THE INVENTION

Formula (1):

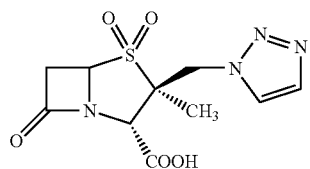

Tazobactam, which is represented by Formula (1) given above, exhibits very weak antibacterial activity, and it is therefore not used alone as an antibacterial agent. However, it irreversively binds to various β-lactamases produced by microorganisms and exhibits an ability to inhibit β-lactamase activities. Hence, tazobactam is used in combination with various existing antibacterial agents that are inactivated by β-lactamases, allowing such antibacterial agents to exhibit their inherent antibacterial activity against β-lactamase-producing microorganisms (Katsuji SAKAI, *Recent Antibiotics Manual*, 10th ed., page 113).

As shown in the reaction scheme below, tazobactam is produced by oxidizing 2α-methyl-2β-[(1,2,3-triazol-1-yl)methyl]penam-3α-carboxylic acid benzhydryl ester (hereinafter sometimes referred to as "TMPB") and de-esterifying the resulting 2α-methyl-2β-[(1,2,3-triazol -1-yl)methyl]penam-3α-carboxylic acid 1,1-dioxide benzhydryl ester (hereinafter sometimes referred to as "TAZB") thus obtained. Therefore, TMPB is of use as an intermediate for synthesizing tazobactam and as a precursor of TAZB.

Reaction Scheme:

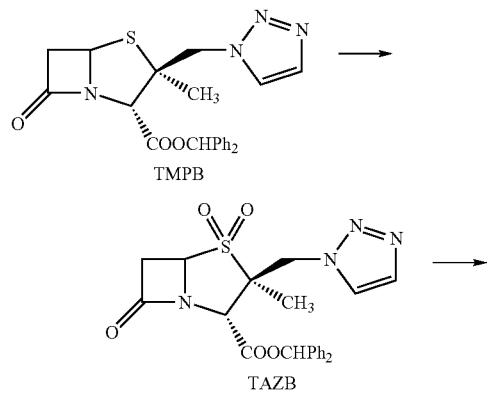

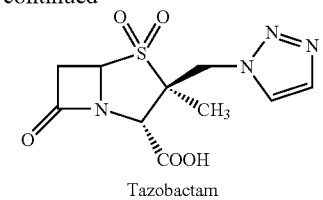

Ph = phenyl

Since the nucleophilic 1,2,3-triazol moiety is contained in the TMPB molecule, oily or amorphous TMPB is unstable and likely to undergo decomposition, degeneration, etc. For this reason, efforts have been made to isolate crystalline TMPB, which is stable (WO02/14325).

The method disclosed in WO02/14325 produces TMPB crystals by concentrating a TMPB-containing solution, diluting the concentrated solution with an acetic acid ester, and mixing the diluted solution with hexane or like solvent.

However, in the method disclosed in WO02/14325, the efficiency of separating TMPB from by-products that are simultaneously generated in the reaction is low. Therefore, to obtain highly pure TMPB crystals, large amounts of TMPB inevitably remain in the mother liquor, resulting in a low yield of TMPB crystals.

DISCLOSURE OF THE INVENTION

An object of the present invention is to provide a process for producing highly pure TMPB in a high yield.

The inventors conducted extensive research to solve the problem described above and, as a result, succeeded in developing novel TMPB-acetone crystals that can be a precursor of TAZB. Furthermore, the inventors found that such TMPB-acetone crystals can be readily produced and efficiently isolated from a solution prepared by concentrating a TMPB-containing solution and dissolving the concentrated solution in acetone, and also found that TMPB crystals can be produced in high purity and high yield by de-acetonizing such TMPB-acetone crystals. The present invention has been accomplished based on these findings.

The present invention is as described in the following Items 1 to 22 below:

1. TMPB-acetone crystals.
2. Crystals according to Item 1 that have a peak at an interplanar spacing of 11.24 to 12.44 Å in the X-ray powder diffraction pattern obtained by copper radiation of $\lambda=1.5418$ Å through a monochromator.
3. Crystals according to Item 1 that have peaks at the following interplanar spacings in the X-ray powder diffraction pattern obtained by a copper radiation of $\lambda=1.5418$ Å through a monochromator:

d (Interplanar Spacings)
   11.24-12.44
   8.41-9.30

4. Crystals according to Item 1 that have peaks at the following interplanar spacings in the X-ray powder diffraction pattern obtained by a copper radiation of $\lambda=1.5418$ Å through a monochromator:

d (Interplanar Spacings)
   11.24-12.44
   8.41-9.30
   7.11-7.87

5.62-6.22
3.78-5.12

5. Crystals according to Item 1 that have peaks at the following interplanar spacings in the X-ray powder diffraction pattern obtained by a copper radiation of $\lambda=1.5418$ Å through a monochromator:

d (Interplanar Spacings)
11.248-12.433
8.413-9.298
7.119-7.868
5.621-6.213
4.632-5.119
4.548-5.026
4.457-4.926
4.206-4.648
4.132-4.567
3.738-4.131
3.785-4.183

6. Crystals according to any one of Items 1 to 5 that have a TMPB/acetone molar ratio of 1/1.

7. A process for producing TMPB-acetone crystals comprising the steps of:
(A) concentrating a TMPB-containing organic solvent solution;
(B) dissolving the resulting concentrate in acetone; and
(C) precipitating TMPB-acetone crystals from the acetone solution thus obtained.

8. A process according to Item 7, wherein the organic solvent in Step A is a halogenated hydrocarbon solvent.

9. A process according to Item 8, wherein the halogenated hydrocarbon solvent is dichloromethane.

10. A process according to any one of Items 7 to 9, wherein in Step (A) the amount of organic solvent is reduced to about 1.5 liters or less per kg of TMPB.

11. A process according to any one of Items 7 to 10, wherein in Step (B) acetone is used in an amount of from about 1.5 to about 5 liters per kg of TMPB contained in the concentrate.

12. A process according to any one of Items 7 to 11, wherein the TMPB-acetone crystals are precipitated by cooling the acetone solution.

13. A process according to any one of Items 7 to 11, wherein the TMPB-acetone crystals are precipitated by adding to the acetone solution a poor solvent for TMPB-acetone crystals.

14. A process according to Item 13, wherein the poor solvent is at least one member selected from the group consisting of $C_{4-8}$ aliphatic hydrocarbons, $C_{4-8}$ alicyclic hydrocarbons and $C_{2-10}$ alkyl ethers.

15. A process according to Item 14, wherein the poor solvent is at least one member selected from the group consisting of n-pentane, n-hexane, n-heptane, n-octane, cyclohexane, diethyl ether, di-n-butyl ether, diisopropyl ether and diisobutyl ether.

16. A process according to Item 15, wherein the poor solvent is n-hexane.

17. A process for producing TAZB comprising the step of reacting TMPB-acetone crystals in a solvent with an oxidizing agent.

18. A process according to Item 17, wherein the oxidizing agent is at least one member selected from the group consisting of permanganic acid, periodic acid, peracetic acid, trifluoroperacetic acid, perbenzoic acid, m-chloroperbenzoic acid, alkali metal salts thereof, and hydrogen peroxide.

19. A process for producing TMPB crystals comprising the step of de-acetonizing TMPB-acetone crystals.

20. A process according to Item 19, wherein the TMPB-acetone crystals subjected to de-acetonization under reduced pressure.

21. A process according to Item 20, wherein the de-acetonization is carried out at a pressure of from about 1 to about 10 kPa and at a temperature of about 20° C. or higher.

22. A process for producing TMPB crystals comprising the steps of:
(A) concentrating a TMPB-containing organic solvent solution;
(B) dissolving the resulting concentrate in acetone;
(C) precipitating TMPB-acetone crystals from the acetone solution thus obtained; and
(D) de-acetonizing the TMPB-acetone crystals.

TMPB-Acetone Crystals

The TMPB-acetone crystals of the present invention can be produced using, for example, Steps (A) to (C) below:

Step A

This step is for concentrating a TMPB-containing organic solvent solution.

TMPB-containing organic solvent solutions usable in this step include TMPB-containing reaction solutions obtained according to known methods.

Organic solvents include those that are usable in reactions for producing TMPB, or in TMPB extraction. Preferable are hydrophobic organic solvents. Examples of such hydrophobic organic solvents are dichloromethane, 1,2-dichloroethane, 1,2-dichloropropane, 1,1,2-trichloroethane, chloroform, carbon tetrachloride, and like halogenated hydrocarbon solvents. Among such solvents, dichloromethane is particularly preferable.

Concentration of TMPB-containing organic solvents can be carried out according to known techniques. Concentration is preferably carried out under reduced pressure, for example, at a pressure of from about 25 to about 80 kPa.

In the present invention, concentration of organic solvent solutions refers to complete removal of organic solvents and partial removal of organic solvents by which organic solvent remains in the concentrate. It is usually sufficient that the amount of organic solvent is concentrated to be not more than about 1.5 liters per kg of TMPB. In view of precipitation efficiency, it is preferably from about 0.15 to about 0.7 liters, and more preferably from about 0.2 to about 0.5 liters, per kg of TMPB.

Step B

This step is for dissolving in acetone the concentrate obtained in Step A.

In this step, it is sufficient that acetone is used in an amount of from 1.5 to 5 liters, preferably from 2 to 4 liters, and more preferably from 2.2 to 3 liters, per kg of TMPB contained in the concentrate. When an organic solvent is present in the concentrate, acetone is preferably used in an amount such that the volume ratio of organic solvent/acetone is not more than 1/3, and preferably not more than 1/4.

In dissolving the aforementioned concentrate in acetone, when the concentrate is heated to aid dissolution, the concentrate should not be heated to a temperature of higher than about 40° C. in view of the stability of TMPB, and it is preferable to avoid heating TMPB for a long time.

Step C

This step is for precipitating TMPB-acetone crystals from the acetone solution obtained in Step B.

Precipitation can be carried out according to conventional precipitation methods. For example, precipitation can be carried out by cooling the acetone solution or adding to the acetone solution a poor solvent for TMPB-acetone crystals.

When crystals are precipitated by cooling the acetone solution, the acetone solution is usually cooled to about 10° C. or lower and preferably about 0° C. or lower.

Solvents that have compatibility with acetone and poor ability to dissolve TMPB are widely used as poor solvents for TMPB-acetone crystals.

Examples of such poor solvents are $C_{4-8}$ aliphatic hydrocarbons, $C_{4-8}$ alicyclic hydrocarbons, $C_{2-10}$ alkyl ethers, etc. Such poor solvents can be used singly or in combination.

Specific examples of $C_{4-8}$ aliphatic hydrocarbons and $C_{4-8}$ alicyclic hydrocarbons are n-pentane, n-hexane, n-heptane, n-octane, cyclohexane, etc.

Specific examples of $C_{2-10}$ alkyl ethers are diethyl ether, diisopropyl ether, di-n-butyl ether, diisobutyl ether, etc.

Among such poor solvents, $C_{4-8}$ aliphatic hydrocarbons are preferable, with n-hexane being particularly preferable.

Although the amount of poor solvent is not limited, in view of precipitation efficiency and workability, it is usually from about 0.1 to about 20 liters, and preferably from about 0.5 to about 5 liters, per liter of acetone contained in the acetone solution.

The precipitation temperature is usually about 56° C. or lower, preferably from about −78 to about 30° C. and more preferably from about −30 to about 10° C.

TMPB-acetone crystals precipitated as above can be separated from the acetone solution according to known filtration methods.

TMPB-acetone crystals thus obtained have a TMPB/acetone molar ratio of 1/1 and exhibit a specific X-ray powder diffraction pattern.

The TMPB-acetone crystals of the invention have a peak at an interplanar spacing of 11.24 to 12.44 Å in the X-ray powder diffraction pattern obtained by copper radiation of $\lambda$=1.5418 Å through a monochromator.

The preferable TMPB-acetone crystals of the invention have peaks at the following interplanar spacings in the X-ray powder diffraction pattern obtained by a copper radiation of $\lambda$=1.5418 Å through a monochromator:

d (Interplanar Spacings)
  11.24-12.44
  8.41-9.30

More preferable TMPB-acetone crystals of the invention have peaks at the following interplanar spacings in the X-ray powder diffraction pattern obtained by a copper radiation of $\lambda$=1.5418 Å through a monochromator:

d (Interplanar Spacings)
  11.24-12.44
  8.41-9.30
  7.11-7.87
  5.62-6.22
  3.78-5.12

Particularly preferable TMPB-acetone crystals of the invention have peaks at the following interplanar spacings in the X-ray powder diffraction pattern obtained by a copper radiation of $\lambda$=1.5418 Å through a monochromator:

d (Interplanar Spacings)
  11.248-12.433
  8.413-9.298
  7.119-7.868
  5.621-6.213
  4.632-5.119
  4.548-5.026
  4.457-4.926
  4.206-4.648
  4.132-4.567
  3.738-4.131
  3.785-4.183

An X-ray diffraction spectral analysis shows that the TMPB-acetone crystals of the invention have a crystalline structure completely different from that of known TMPB crystals. A $^1$H-NMR spectral analysis shows the presence of TMPB at a TMPB/acetone molar ratio of 1/1. A thermogravimetric analysis also reveals the presence of TMPB and acetone at a molar ratio of 1:1 and the occurrence of acetone elimination at a temperature (83.2° C.) higher than the boiling point of acetone. Therefore, it is presumed that acetone is not adhered to TMPB due to insufficient drying, but that acetone is present throughout the crystal lattice of TMPB, thereby forming a clathrate.

TAZB Production

TAZB is produced by reacting the TMPB-acetone crystals of the invention with an oxidizing agent in a solvent.

Known oxidizing agents can be widely used, and examples thereof are permanganic acid, periodic acid, peracetic acid, trifluoroperacetic acid, perbenzoic acid, m-chloroperbenzoic acid, alkali metal salts thereof, and hydrogen peroxide. Alkali metals as used herein include sodium, potassium, etc. Such oxidizing agents can be used singly or in combination.

Although such oxidizing agent may be used in a large excess relative to the TMPB-acetone crystals, it is usually sufficient to use the oxidizing agent in an amount of 1 to 5 moles per mole of the TMPB-acetone crystals.

Examples of the solvent are dichloromethane, chloroform, carbon tetrachloride and like halogenated hydrocarbons; tetrahydrofuran, dioxane and like ethers; acetone, methyl ethyl ketone and like ketones; acetic acid, formic acid and like organic acids; pyridine; water, etc. Such solvents can be used singly or in combination.

Such solvents are usually used in an amount of from about 0.001 to about 100 liters, and preferably from about 0.01 to about 10 liters, per kg of TMPB-acetone crystals, but the amount of the solvent is not limited to the above range.

Although the temperature for reaction with oxidizing agents is not limited, about 0 to about 60° C. is usually sufficient. The reaction time is usually from about 0.5 to about 12 hours.

TAZB thus produced can be purified according to conventional purification methods such as extraction, column chromatography, recrystallization, etc.

TMPB Crystal Production

The TMPB-acetone crystals of the invention very slowly change to TMPB crystals at atmospheric pressure and room temperature (20° C.). To produce highly pure TMPB crystals such that TMPB-acetone crystals cannot be detected, it is preferable to carry out de-acetonization.

De-acetonization may be carried out by, for example, maintaining the TMPB-acetone crystals under reduced pressure. Although the extent of pressure reduction is not limited, a pressure of, for example, from about 1 to about 10 kPa, and preferably from about 1.3 to about 5 kPa, is sufficient. It is further preferable to maintain the ambient temperature of the TMPB-acetone crystals usually at about 20° C. or higher, preferably 30° C. or higher and more preferably from about 30 to about 40° C. Excessively high ambient temperatures possibly result in degradation of the TMPB crystals.

The de-acetonization time cannot be generalized since it varies depending on the extent of pressure reduction, temperature, etc. For example, de-acetonization takes 6 hours or longer at about 4 kPa and about 40° C.

EFFECTS OF THE INVENTION

One of the advantages of the process for producing TMPB-acetone crystals of the present invention is its great crystallization efficiency. It is presumed that TMPB in acetone forms a clathrate in conjunction with acetone, which is distinct from TMPB alone, and thereby the compatibility with acetone is decreased and TMPB-acetone crystals are more readily precipitated.

Therefore, in the production of the TMPB-acetone crystals of the invention, the precipitation temperature is not limited, allowing sufficient precipitation to occur at room temperature. Moreover, cooling does not permit contamination by other components or separation of oily material.

The TMPB-acetone crystals of the invention can be used as they are in the production of TAZB.

Moreover, TMPB crystals can be readily produced by de-acetonizing the TMPB-acetone crystals of the invention. In particular, TMPB crystals can be produced in high yield and high purity by forming crystals composed of TMPB and acetone, which can be recovered extremely efficiently, and then de-acetonizing the TMPB-acetone crystals.

According to the process for producing TMPB crystals of the invention, TMPB crystals are produced by way of producing TMPB-acetone crystals, which can be efficiently precipitated, thereby not allowing contamination with by-product cepham compounds and readily enabling TMPB crystals to be obtained from TMPB-acetone crystals.

Therefore, the method of the invention is highly industrially advantageous.

BEST MODE FOR CARRYING OUT THE INVENTION

Figure 1:
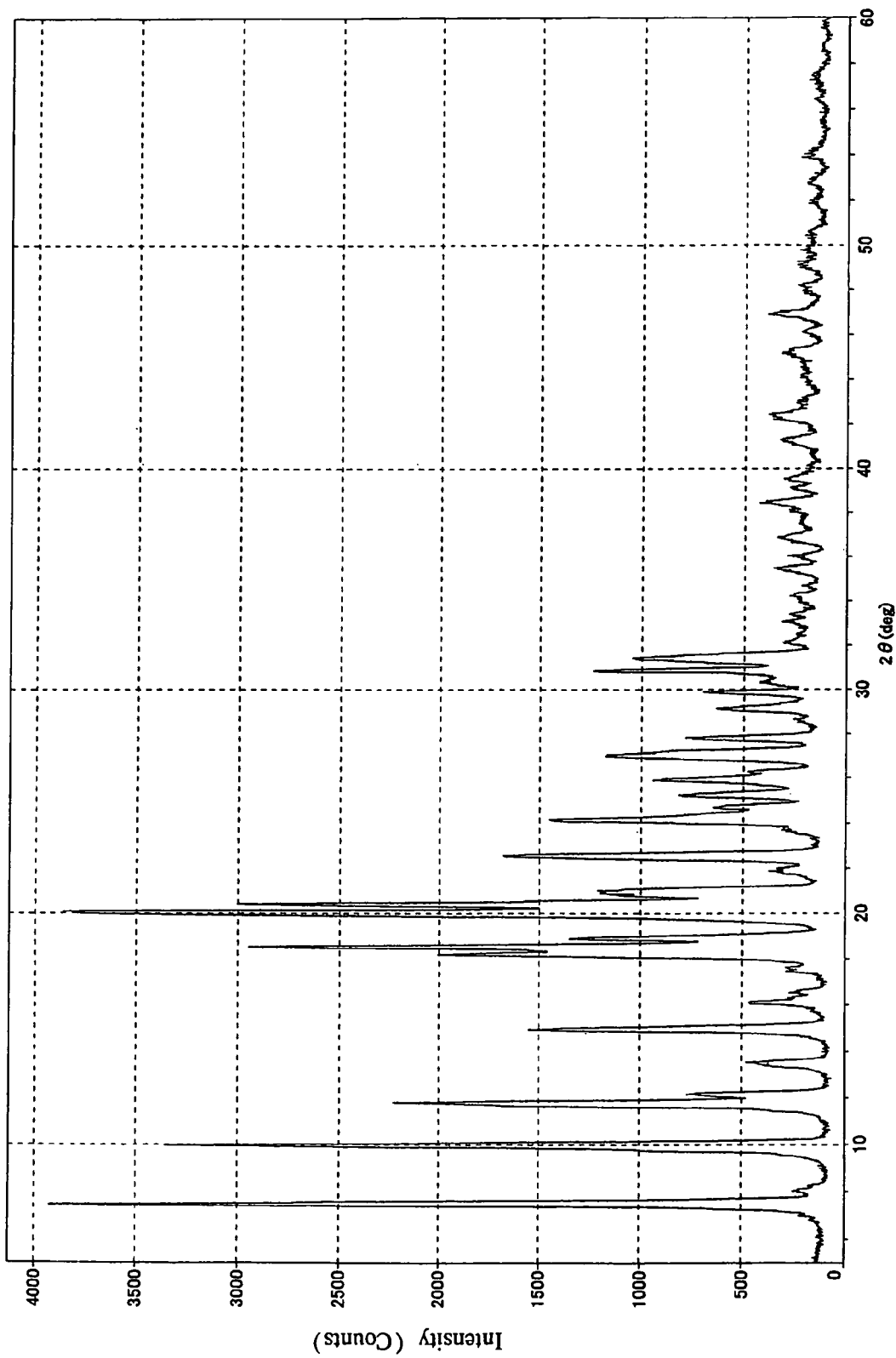
FIG. 1 is the x-ray powder diffraction pattern of the crystals obtained in Example 1.

Examples and a Comparative Example are given below to describe the invention in more detail. However, the scope of the invention is not limited to or by these examples.

Example 1

A dichloromethane solution (700 ml) containing 43.5 g of 2β-chloromethyl-2α-methylpenam-3-carboxylic acid benzhydryl ester was mixed with 200 ml of 1,2,3-triazole and about 130 ml of an anion exchange resin ("Diaion WA30", manufactured by Mitsubishi Chemical Corp.), and the mixture was stirred at 40° C. for 3 hours. After the reaction, the anion exchange resin was filtered off, and 200 ml of water was added to the filtrate to separate the dichloromethane layer. The dichloromethane layer thus obtained was washed twice with water, thereby giving 600 ml of a dichloromethane solution. This dichloromethane solution is hereinafter referred to as "dichloromethane solution (1)". This solution contained 30 g of TMPB.

Dichloromethane solution (1) was concentrated under reduced pressure (60 to 40 kPa) at 40° C. or lower. When about 450 ml of dichloromethane was removed, 250 ml of acetone was added to the thus-concentrated dichloromethane solution (1). Concentration was continued until the amount of the solution reached about 100 ml. A gas chromatographic analysis revealed about 30 ml of acetone and about 15 ml of dichloromethane. To this solution was added acetone in such an amount that the total amount of acetone in the resulting solution was 80 ml. This solution is hereinafter referred to as "acetone solution (1)".

Acetone solution (1) was cooled to −20° C. and stirred. After sufficient crystal precipitation, the crystals precipitated were recovered by filtration and washed with 80 ml of acetone/n-hexane mixture (volume ratio=1:1).

According to the $^1$H-NMR spectrum, these crystals were composed of TMPB and acetone and the moler ratio of TMPB to acetone was 1:1.

Appearance: white crystals

Amount recovered: 30 g

Yield: 90% (based on TMPB contained in dichloromethane solution (1))

$^1$H-NMR (300 MHz, CDCl$_3$, δppm): 1.20 (3H, s), 2.16 (6H, s), 3.17 (1H, ABq, J=16.2 Hz), 3.66 (1H, ABq, J=16.2 Hz), 4.58 (1H, ABq, J=14.7 Hz), 4.59 (1H, ABq, J=14.7 Hz), 4.87 (1H, s), 5.41 (1H, dd, J=4.2 Hz, 1.5 Hz), 6.90 (1H, s), 7.2-7.4 (10H, m), 7.73 (2H, d, J=3.9 Hz)

X-ray powder diffraction pattern (obtained with copper radiation of λ=1.5418 Å through a monochromator, same applies hereinbelow):

| d (Interplanar spacings) | Relative intensities (I/I$_0$) |
|---|---|
| 11.8405 | 96 |
| 8.8556 | 84 |
| 7.4935 | 55 |
| 7.2487 | 18 |
| 6.5438 | 10 |
| 5.9170 | 38 |
| 5.5005 | 10 |
| 4.8756 | 49 |
| 4.7869 | 76 |
| 4.6915 | 33 |
| 4.4271 | 100 |
| 4.3498 | 75 |
| 4.2630 | 26 |
| 4.2149 | 27 |
| 3.9345 | 42 |
| 3.6837 | 36 |
| 3.6014 | 13 |
| 3.5283 | 18 |
| 3.4346 | 21 |
| 3.2996 | 28 |
| 3.2734 | 21 |
| 3.2065 | 17 |
| 3.0640 | 13 |
| 2.9878 | 14 |
| 2.8951 | 29 |
| 2.8554 | 19 |
| 2.8448 | 24 |

Purity: 100% (determined by using liquid chromatography)

FIG. 1 shows the X-ray powder diffraction pattern of the crystals obtained above.

Example 2

Acetone solution (1) was prepared in the same manner as in Example 1.

Acetone solution (1) was heated to 38° C., and 80 ml of n-hexane was added dropwise, thereby precipitating crystals. This crystal-containing solution was cooled to −20° C. and stirred. After sufficient crystal precipitation, the crystals precipitated were recovered by filtration and washed with 80 ml of acetone/n-hexane mixture (volume ratio=1:1).

Since the $^1$H-NMR spectrum of the crystals thus obtained was identical to that of the crystals of Example 1, the crystals were verified to be of TMPB-acetone.

Appearance: white crystals
Purity: 100% (determined by using liquid chromatography)
Amount recovered: 32 g
Yield: 97% (based on TMPB contained in dichloromethane solution (1))

Examples 3-7

TMPB-acetone crystals were prepared in the same manner as in Example 2 except that various poor solvents as shown in Table 1 below were used in place of n-hexane.

Since the $^1$H-NMR spectra of the crystals thus obtained were identical to that of the crystals of Example 1, the crystals were verified to be of TMPB-acetone.

TABLE 1

|       | Poor solvent    | Yield (based on TMPB contained in dichloromethane solution (1)) |
|-------|-----------------|-----------------|
| Ex. 3 | Cyclohexane     | 80.5%           |
| Ex. 4 | n-Pentane       | 81.8%           |
| Ex. 5 | n-Octane        | 82.9%           |
| Ex. 6 | Diisopropyl ether | 75.1%         |
| Ex. 7 | Di-n-butyl ether | 83.8%          |

Example 8

TMPB-acetone crystals (30 g) as obtained in Example 1 were left to stand at 40° C. under reduced pressure (4 kPa) for 8 hours. Based on the $^1$H-NMR spectrum, the crystals thus obtained were of TMPB, with no TMPB-acetone crystals being contained in the TMPB crystals.

Appearance: white crystals
Amount recovered: 27 g
Yield: 90% (based on TMPB contained in dichloromethane solution (1))

X-ray powder diffraction pattern:

| d (Interplanar spacings) | Relative intensities (I/I$_0$) |
|---|---|
| 9.5016 | 81 |
| 7.5574 | 73 |
| 6.3658 | 20 |
| 5.5623 | 11 |
| 5.0578 | 100 |
| 4.8545 | 54 |
| 4.7412 | 56 |
| 4.6866 | 43 |
| 4.5577 | 19 |
| 4.4140 | 34 |
| 4.3330 | 44 |
| 4.2308 | 47 |
| 3.9974 | 25 |
| 3.7857 | 10 |
| 3.6777 | 20 |
| 3.6014 | 29 |
| 3.1907 | 11 |
| 3.0995 | 11 |
| 2.8483 | 11 |

Purity: 100% (determined by using liquid chromatography)

Figure 2:
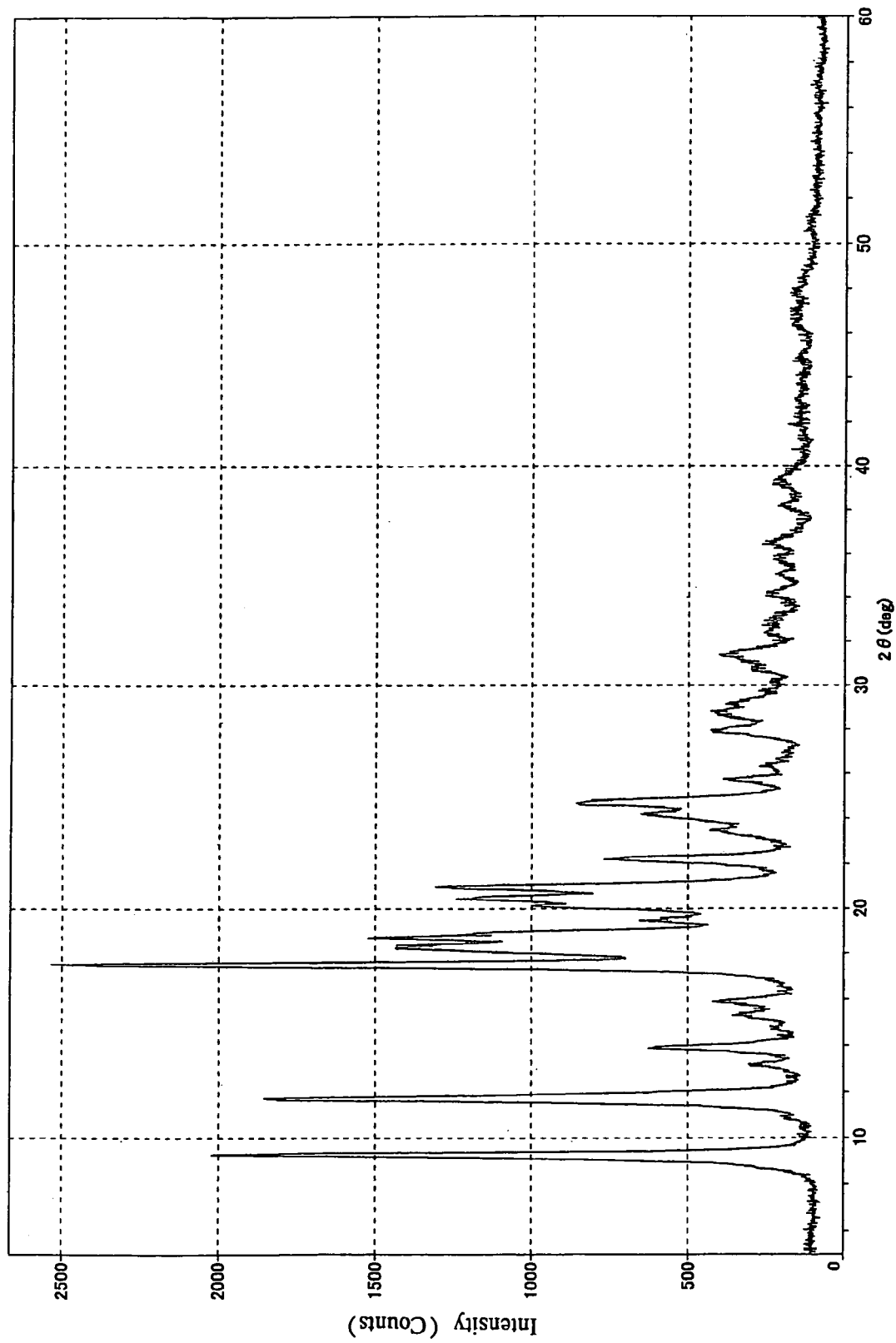
FIG. 2 is the x-ray powder diffraction pattern of the crystals obtained in Example 8.

FIG. 2 shows the X-ray powder diffraction pattern of the crystals.

Example 9

TMPB-acetone crystals (32 g) as obtained in Example 2 were treated in the same manner as in Example 8. Based on the $^1$H-NMR spectrum, the crystals thus obtained were of TMPB, and the $^1$H-NMR spectrum and the x-ray powder diffraction pattern thereof were identical to those of the crystals prepared in Example 8.

Appearance: white crystals
Amount recovered: 29 g
Yield: 97% (based on TMPB contained in dichloromethane solution (1))
Purity: 100% (determined by using liquid chromatography)

Example 10

TMPB-acetone crystals (32 g) as obtained in Example 1 were dissolved in 240 ml of dichloromethane, and 68 ml of acetic acid was added thereto. To this mixture was added little by little 20.4 g of potassium permanganate without the temperature of the mixture exceeding 20° C., and the mixture was stirred for 3 hours while making sure that the temperature of the mixture did not exceed 40° C. After completion of the reaction, 300 ml of dichloromethane was added. The mixture thus obtained was cooled to 5° C., and 35% hydrogen peroxide aqueous solution was added until the color of the mixture disappeared. The dichloromethane layer was separated, washed with 2% aqueous sodium hydrogensulfite solution and then with water, and dried over magnesium sulfate. The dichloromethane layer was concentrated, and methanol was added to the residue to effect crystallization, thereby giving the desired TAZB.

Amount recovered: 29.7 g
Yield: 96%
Purity: 100% (determined by using liquid chromatography)

Comparative Example 1

The procedure of Example 1 was repeated to obtain dichloromethane solution (1).

Dichloromethane solution (1) was concentrated under reduced pressure (60 to 40 kPa) at 40° C. When the amount of removed dichloromethane reached about 420 ml, 86 ml of ethyl acetate was added. Concentration was continued until the amount of removed organic solvent reached 120 ml. The concentrated solution was analyzed by gas chromatography, and diluted with dichloromethane and ethyl acetate to have a dichloromethane content of 20 ml and an ethyl acetate content of 80 ml. To this diluted solution was added 48 ml of n-hexane while maintaining the solution temperature at 22° C. or higher, thereby precipitating TMPB crystals.

The crystals were recovered by filtration, washed with 80 ml of ethyl acetate/n-hexane mixture (volume ratio=1:1), and dried under reduced pressure at about 40° C.

Appearance: pale yellow crystals
Amount recovered: 19 g
Yield: 63.3%

The invention claimed is:

1. 2α-methyl-2β[(1,2,3-triazol-1-yl)methyl]penam-3α-carboxylic acid benzhydryl ester-acetone crystals.

2. Crystals according to claim 1 that have a peak between an interplanar spacing of 11.24 to 12.44 Å in the X-ray powder diffraction pattern obtained by copper radiation of $\lambda=1.5418$ Å through a monochromator.

3. A process for producing 2α-methyl-2β-[(1,2,3-triazol-1-yl)methyl]penam-3α-carboxylic acid benzhydryl ester-acetone crystals comprising the steps of:
(A) concentrating a hydrophobic organic solvent solution containing 2α-methyl-2β-[(1,2,3-triazol-1-yl)methyl]penam-3α-carboxylic acid benzhydryl ester;
(B) introducing the resulting concentrate to acetone; and
(C) precipitating 2α-methyl-2β-[(1,2,3-triazol-1-yl)methyl]penam-3α-carboxylic acid benzhydryl ester-acetone crystals from the acetone solution thus obtained.

4. A process for producing 2α-methyl-2β-[(1,2,3-triazol-1-yl)methyl]penam-3αi-carboxylic acid 1,1-dioxide benzhydryl ester comprising the step of reacting in a solvent an oxidizing agent with 2α-methyl-2β-[(1,2,3-triazol-1-yl)methyl]penam-3α-carboxylic acid benzhydryl ester-acetone crystals.

5. A process for producing crystals of 2α-methyl-2β-[(1,2,3-triazol-1-yl)methyl]penam-3α-carboxylic acid benzhydryl ester comprising the step of de-acetonizing by maintaining the TMPB-acetone crystals under reduced pressure, 2α-methyl-2β-[(1,2,3-triazol-1-yl)methyl]penam-3α-carboxylic acid benzhydryl ester-acetone crystals.

6. A process for producing crystals of 2α-methyl-2β-[(1,2,3-triazol-1-yl)methyl]penam-3α-carboxylic acid benzhydryl ester comprising the steps of:
(A) concentrating a hydrophobic organic solvent solution containing 2α-methyl-2β-[(1,2,3-triazol-1-yl)methyl]penam-3α-carboxylic acid benzhydryl ester;
(B) introducing the resulting concentrate in acetone;
(C) precipitating 2α-methyl-2β-[(1,2,3-triazol-1-yl)methyl]penam-3α-carboxylic acid benzhydryl ester-acetone crystals from the acetone solution thus obtained; and
(D) de-acetonizing by maintaining the TMPB-acetone crystals under reduced pressure, the 2α-methyl-2β-[(1,2,3-triazol-1-yl)methyl]penam-3α-carboxylic acid benzhydryl ester-acetone crystals.

7. A process for producing crystals according to claim 6, wherein the red LAced pressure is from 1 to 10 kPa.

8. A process for producing crystals according to claim 6, wherein the reduced pressure is maintained at a temperature of 20° C. or higher.

9. A process for producing crystals according to claim 5, wherein the reduced pressure is from 1 to 10 kPa.

10. A process for producing crystals according to claim 5, wherein the reduced pressure is maintained at a temperature of 20° C. or higher.

* * * * *